(12) United States Patent
Jem

(10) Patent No.: US 6,455,287 B1
(45) Date of Patent: Sep. 24, 2002

(54) MECHANICAL DISRUPTION OF BACTERIAL CELLS FOR PLASMID RECOVERY

(75) Inventor: Kwan-Min Jim Jem, Berwyn, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 08/393,321

(22) Filed: Feb. 23, 1995

(51) Int. Cl.$^7$ ............................................... C12N 13/00
(52) U.S. Cl. ............................... 435/173.7; 435/173.1; 435/173.4; 435/259
(58) Field of Search .......................... 435/173.7, 173.4, 435/173.1, 259

(56) References Cited

U.S. PATENT DOCUMENTS

| | | | |
|---|---|---|---|
| 4,533,254 A | 8/1985 | Cook et al. | 366/176 |
| 5,221,737 A | 6/1993 | Bartsch et al. | 536/23.2 |
| 5,310,652 A | 5/1994 | Gelfand et al. | 435/6 |

OTHER PUBLICATIONS

Agerkvist, I. et al., "Characterization of *E. coli* Cell Disintegrates from a Bead Mill and High Pressure Homogenizers", *Biotechnology and Bioengineering* 1990, 36, 1083–1089.

Asenjo, J., "Cell Disruption and Removal of Insolubles", *Separation for Biotech* 1990, pp. 11–20.

Chakrabarti, A. et al., A Procedure for large–Scale Plasmid Isolation without Using Ultracentrifugation, *Biotechnology and Applied Biochemistry* 1992, 16, 211–215.

Chandra, G. et al., "Large–Scale Purification of Plasmid DNA by Fast Protein Liquid Chromatography Using a Hi–Load Q Sepharose Column", *Analytical Biochemistry* 1992, 203, 169–172.

Chisti, Y. and Young, "Disruption of Microbial Cells for Intracellular Products", *Enzyme Microb. Technol.* 1986, 8, 194–204.

"Currents Protocols in Molecular Biology", Ausubel et al., ed. vol. 1, Chap. 1, pages of Sections 1.6 and 1.7, Green/Wiley & Sons, 1993.

Dakubu, S., "Cell Inactivation by Ultrasound", *Biotechnology and Bioengineering* 1976, 18, 465–471.

Deininger, P., "Random Subcloning of Sonicated DNA: Application to Shotgun DNA Sequence Analysis", *Analytical Biochemistry* 1983, 129, 216–223.

Doulah, M., "Mechanism of Disintegration of Biological Cells in Ultrasonic Cavitation", *Biotechnology and Bioengineering* 1977, 19, 649–660.

Fechheimer, M. et al., "Transfection of Mammalian Cells with Plasmid DNA by Scrape Loading and Sonication Loading", *PNAS USA* 1987, 84, 8463–8467.

Harrison, S. et al., "The Effect of Culture History on the Disruption of *Alcaligenes Eutrophus* By High Pressure Homogenisation", *Separations for Biotech* 1990, 38–47.

Johnson, J., "Isolation and Purification of Nucleic Acids", in "Nucleic Acid Techniques in Bacterial Systematics", Stackebrandt, ed., John Wiley & Sons, Chichester, 1991.

Kula, M., "Purification of Proteins and the Disruption of Microbial Cells", *Biotechnology Progress* 1987, 3(1), 31–42.

Limon–Lason, J. et al., "Reactor Properties of a High–Speed Bead Mill for Microbial Cell Rupture", *Biotechnology and Bioengineering* 1979, 21, 745–774.

Marffy, F. and Kula, "Enzyme Yields form Cells of Brewer's Yeast Disrupted by Treatment in a Horizontal Disintegrator", *Biotechnology and Bioengineering* 1974, 16, 623–634.

Mosqueira, F. et al., "Characteristics of Mechanically Disrupted Bakers' Yeast in Relation to its Separation in Industrial Centrifuges", *Biotechnology and Bioengineering* 1981, 23, 335–343.

Naglak, T. and Wang, "Protein Release from the Yeast *Pichia pastoris* by Chemical Permeabilization: Comparison to Mechanical Disruption and Enzymatic Lysis", *Separations for Biotech* 1990, 55–64.

Neppiras, E. and Hughes, "Some Experiments on the Disintegration of Yeast by High Intensity Ultrasound", *Biotechnology and Bioengineering* 1964, 6, 247–270.

Sambrook et al., "Extraction and Purification of Plasmid DNA" Section 1.21–1.51 in "Molecular Cloning: A Laboratory Manual", 2nd Ed., Cold Spring Harbor Press, 1989.

Sauer, T. et al., "Disruption of Native and Recombinant *Escherichia coli* in a High–Pressure Homogenizer", *Biotechnology and Bioengineering* 1989, 33, 1330–1342.

Schutte, H. et al., "Experiences with a 20 Litre Industrial Bead Mill for the Disruption of Microorganisms", *Enzyme Microb. Technol.* 1983, 5, 143–148.

Ulmer, J. et al., "Heterologous Protection Against Influenza by Injection of DNA Encoding a Viral Protein", *Science* 1993, 259, 1745–1749.

Wang, B. et al., "Gene Inoculation Generates Immune Responses Against Human Immunodeficiency Virus Type 1", *PNAS USA* 1993, 90, 4156–4160.

Wheelwright, S., "Protein Purification: Design and Scale up of Downstream Processing", Chap. 6, pp. 63, 64, 66, 67–70, Oxford University Press, 1991.

Woodrow, J. and Quirk, "Evaluation of the Potential of a Bead Mill for the Release of Intracellular Bacterial Enzymes", *Enzyme Microb. Technol.* 1982, 4(6), 385–389.

*Primary Examiner*—Leon B. Lankford, Jr.
(74) *Attorney, Agent, or Firm*—Howson and Howson

(57) ABSTRACT

The recovery yields of intact plasmids from bacterial cells mechanically disrupted by various methods were measured. Bacterial cell disruption through bead milling and microfluidization were found to achieve the greatest recovery of intact plasmid. Other methods resulted in substantial DNA plasmid degradation.

26 Claims, 6 Drawing Sheets

MECHANICAL DISRUPTION OF BACTERIAL CELLS FOR PLASMID RECOVERY

CROSS-REFERENCE TO RELATED PATENT APPLICATION

This application is a Continuation-in-part application of Ser. No. 08/286,132 filed Aug. 4, 1994, now abandoned.

FIELD OF THE INVENTION

This invention relates to methods of cell disruption and plasmid extraction in the field of recombinant DNA technology. Specifically, it relates to mechanical methods of rupturing cells to release intact plasmids cloned within the cells.

BACKGROUND OF THE INVENTION

In the field of recombinant DNA technology, plasmid expression vectors are routinely employed to express foreign proteins. A number of recombinant proteins, including recombinant human insulin (HUMULIN®, Lilly), recombinant human erythropoietin (EPOGEN®, Amgen), recombinant tissue plasminogen activator (ACTIVASE®, Genentech), and recombinant α interferon (ROFERON®, Roche), are now available for human pharmaceutical use, and commercial scale methods have been developed for recovery and purification of recombinant proteins from cell culture and/or microbial fermentation. For most of recombinant proteins produced in mammalian cell culture and for some recombinant proteins produced in microbes but secreted into the culture medium, cell disruption is not required for the recovery of these products. When cell disruption is required to release intracellular recombinant products from microbes, mechanical cell rupture methods are frequently used in such large recombinant protein recovery processes.

More recently, it has been shown that plasmid DNA may be useful as a non-viral nucleic acid delivery vehicle for clinical applications. (See, e.g., Wang et al., *Proc. Nat'l Acad. Sci. USA* 90:4156–4160 (1993); Ulmer et al., *Science* 259:1745–1749 (1993)). For such applications, which include gene therapy and genetic immunization, the plasmids themselves rather than the expressed proteins are the desired therapeutic product. Accordingly, there is a need for pharmaceutically acceptable large scale processes for recovery of intact plasmid DNA. For a number of reasons, mechanical cell disruption methods are preferred to chemical or enzymatical cell disruption methods if the yields are comparable.

Bacterial plasmids are double-stranded closed circular DNA molecules that range in size from about 1 kb to more than 200 kb. They are found in a variety of bacterial species, where they serve as accessary genetic units that replicate and are inherited independently of the bacterial chromosome. Plasmids can be produced via bacterial fermentation and recovered by cell disruption and plasmid recovery operations. Fermentation technology to produce plasmids is relatively well understood, and a number of laboratory scale methods useful for bacterial cultures ranging in size from 1 mL to 1 L have been developed to purify plasmid DNA from bacteria. (See Sambrook, Fritsch and Maniatis, Section 1.21, "Extraction and Purification of Plasmid DNA", *Molecular Cloning: A Laboratory Manual*, Second Edition, Cold Spring Harbor Laboratory Press (1989).) These methods involve the growth of the bacterial culture and replication of plasmid; harvesting and lysis of the bacteria; isolation and purification of plasmid DNA.

Following growth of the bacterial culture, bacteria are normally recovered by centrifugation and lysed by one of a number of methods, including treatment with enzymes, nonionic or ionic detergents, organic solvents, alkali, or heat. The choice of lytic method is influenced by factors such as the size of the plasmid, the strain of bacteria used, and methods to be used subsequently to purify the plasmid DNA. Although well suited for small scale processes, enzymatic or chemical lysis are rather expensive. Chemical lysis also limits the choice of the downstream processing techniques used subsequently to purify the plasmid DNA. Enzymatic lysis frequently uses animal-derived enzymes such as lysozyme, which maybe accompanied with animal virus. Significant efforts to validate the removal of any possible viral contaminations are needed for this situation.

The currently published laboratory methods are in general unsatisfactory for large scale plasmid purification processes. Laboratory methods for isolation and purification of plasmids from bacterial culture frequently use dangerous organic solvents and chemicals such as cesium chloride and ethidium bromide, which are in general unacceptable for human pharmaceutical use. The few studies related to large scale plasmid recovery that have been reported, (See Chandra, G. et al., *Analytical Biochemistry* 203:169–172 (1992); Chakrabarti, A. et al., *Biotechnology and Applied Biochemistry* 16:211–215 (1992)), use chemical methods of cell lysis, i.e., alkaline-SDS lysis. However, SDS can cause significant problems in downstream purification.

SUMMARY OF THE INVENTION

In general laboratory scale plasmid purification methods were developed for gene cloning purposes, in which case, bacterial genomic DNA and tRNA or rRNA impurities as well as damaged plasmid are relatively unimportant. In contrast, plasmid DNA for pharmaceutical use must meet extremely high standards of identity and purity; this necessitates stringent limits on nucleic acid and protein impurities. Non-plasmid DNA, RNA, as well as plasmid DNA fragments may need to be removed in the downstream purification process. As intact plasmid DNA is ordinarily separable from both the larger intact host cell genomic DNA and from smaller cellular RNAs and DNAs on the basis of size and chemistry, it is important to avoid shearing either the plasmid DNA or the genomic DNA of the host organism. Linearized plasmid DNA and genomic DNA fragments similar in size to the intact plasmid product may be particular difficult to remove.

Bacterial plasmids for clinical applications typically contain large segments of product DNA (mammalian DNA for gene therapy applications or pathogen DNA for genetic immunization), as well as the expression vectors themselves, which contain the genes for selection in bacteria, the sequences for replication in bacteria, and the regulatory elements for expression in mammalian cells. Such plasmid molecules tend to be large, on the order of $10^6$–$10^7$ Daltons (5–20 kb), which is approximately two to three orders of magnitude larger than typical recombinant protein products (e.g., human growth hormone at $10^4$ Dalton). Large plasmids (greater than 10 kb size) are particularly susceptible to damage, especially by physical forces that might be necessary to release the plasmid from the interior of the cell.

Although mechanical methods of cell disruption would be more economical and easier to carry out, and therefore preferred to enzymatic or chemical cell disruption methods for large scale processes, it is recognized that mechanical methods may damage DNA at the same time as the cells are broken. (Wheelwright, S. M., *Protein Putification:Design and Scale up of Downstream Processing*, Oxford University Press (1991), in Chapter 6: Cell Disruption, p. 63. This presents a significant potential problem for pharmaceutical use, where intact, functional plasmid DNA is required and supercoiled plasmid DNA is preferred. Plasmid DNA which has been "nicked" but not cut through both strands, loses it supercoiled configuration and becomes "relaxed" circular DNA. Supercoiled plasmid DNA, which is smaller and more compact than relaxed closed circular plasmid DNA and less vulnerable to enzymatic degradation, expresses better than either relaxed circular or linear DNA. Although supercoiled plasmid DNA is preferred, both supercoiled and relaxed circular plasmid DNA are likely to express the gene of interest and are considered "intact" plasmid DNA. Although plasmid linearized using a selected restriction enzyme may constitute a functional expression unit, mechanical forces are likely to cut or break plasmid in a random manner. Randomly linearized plasmid DNA and broken or fragmented plasmid DNA are considered damaged and are likely to be ineffective or nonfunctional for pharmaceutical purposes. Not only is such damaged plasmid DNA ineffective, it will probably need to be removed in downstream processing to achieve a higher standard of purity. To permit recovery of intact plasmid DNA, processing conditions must be very mild, particularly with respect to shear forces. Although enzymatic and chemical lysis methods tend to involve little or no shear force, it presents other problems as discussed previously. Various methods of cell lysis, including certain mechanical methods, are available when it is not necessary to obtain intact plasmid DNA; however, the development of pharmaceutically acceptable large scale procedures for mechanical cell disruption yielding intact plasmid DNA presents a substantial challenge for biochemical engineers.

Several processing methods for the disruption of bacterial cells are commonly used to release intracellular protein products. These include: 1) sonication (Neppiras, E. A. and Hughes, D. E., "Some experiments on the disintegration of yeast by high intensity sound", *Biotechnology and Bioengineering*, 6:247–270 (1964)); 2) homogenization (Kula, M.-R. and Schutte, H., "Purification of proteins and the disruption of microbial cells", *Biotechnology Process* 3(1):31–42 (1987)); 3) microfluidization (Sauer, T., Robinson, C. W., and Glick, B. R., "Disruption of native and recombinant *Escherichia coli* in a high pressure homogenizer", *Biotechnology and Bioengineering*, 33:1330–1342 (1989)); Agerkvist, I., and Enfors, S.-O., "Characterization of *E. coli* cell disintegrates from a bead mill and high pressure homogenizers", *Biotechnology and Bioengineering* 36:1083–1089 (1990); 4) bead milling (Kula and Schutte, supra; Limon-Lason, J., Hoare, M., Osborn, C. B., Doyle, D. J., and Dunnill, P., "Reactor properties of a high speed bead mill for microbial cell rupture", *Biotechnology and Bioengineering* 21(5):745–774 (1979); Marffy, F. and Kula, M. R., "Enzyme yields from cells of brewers yeast disrupted by treatment in a horizontal disintegrator", *Biotechnology and Bioengineering* 16:632–634 (1974)); and more recently 5) nebulization. The effectiveness of these processes has been studied to a limited extent when intracellular proteins were the product of interest or when cell disruption was the only goal (Marffy and Kula, supra; Woodrow, J. R. and Quirk, A. V., "Evaluation of the potential of a bead mill for the release of intracellular bacterial enzymes", *Enzyme and Microbial Technology* 4(6):385–389 (1982); and Schutte, H., Kroner, K. H., Hustedt, H., and Kula M. R., "Experiences with a 20 liter industrial bead mill for the disruption of microorganisms", *Enzyme and Microbial Technology* 5(2):143–148 (1983)). The findings show that all of the above mentioned methods are effective for bacterial cell disruption and that the disruption depends on the conditions of residence time, pressure, agitation rate, and other equipment variables as appropriate for the particular device. The major difference between the different methods is related to the size of the cell fragments generated, with some of the methods disrupting cells with less overall destruction of the cell envelope. This is significant since the size of the fragments generated has an important impact on further downstream processing when these particles are removed from the lysate or, minimally, separated from other subcellular species. (Agerkvist and Enfors, supra, and Mosqueira, F. G., Higgins, J. J., Dunnill, P. and Lilly, M. D., "Characteristics of mechanically disrupted baker's yeast in relation to its separation in industrial centrifuges", *Biotechnology and Bioengineering* 23:335–343 (1981)).

In addition to the effect of processing on the size of the cell fragments generated, some studies have shown that the severity of the cell disruption conditions can have an impact on the yield of active protein recovered in the process. (Marffy and Kula, supra.) Generally speaking, the amount of active protein found in the liquid phase (i.e., outside the cells) increases in proportion to the fraction of cells disrupted early in the disruption process, but then decreases with further processing. This behavior fits a model of the process in which the protein is released from the cells by disruption by a first order process (Dakubu, S., "Cell Inactivation by Ultrasound", *Biotechnology and Bioengineering* 18:465–471 (1979); Marffy and Kula, supra; Limon-Lason, et al., supra), then is deactivated by the effects of the disruption process. There seems to be general agreement that protein deactivation is caused by shearing at the molecular level or by thermal denaturation caused by local overheating of the suspension fluid (Marffy and Kula, supra; Chisti and Moo-Young, 1986, "Disruption of Microbial Cells for Intracellular Products", *Enzyme & Microbial Technology* 8:194–204 (1986)). However, it is also clear that different proteins behave quite differently, i.e., some are easily deactivated and suffer severely from overprocessing, while others are more stable and are persistent in the product. Determination of acceptable processing techniques is primarily empirical and involves systematic manipulation of the severity of the disruption, the residence time, and the number of passes or amount of reprocessing of the cell suspension. Optimization of recovery processes generally involves the assumption that the disruption and deactivation processes can be modeled as sequential first order reactions. This suggests certain disruption motifs, such as avoiding well stirred reactors which tend to minimize intermediate product formation, and optimization of reactor residence time and pseudo rate constants. Little work has been done to confirm the behavior of actual systems.

To the extent that the effects of mechanical cell disruption on cellular DNA have been evaluated, DNA fragmentation has in general been considered desirable in that it reduces the viscosity of the solution, thereby making protein recovery easier. (Agerkvist and Enfors, supra). In contrast to protein isolation studies, few if any studies have been conducted on cell disruption processes when DNA is the final product to be recovered. Although the general problem is similar to that with protein release, in that the processes required to disrupt the cells also tend to destroy the product molecule, because the DNA tends to be a larger molecule, it is much more sensitive to shear generated in most disruption methods than are proteins. For this reason, the destruction process can be very rapid, and the yields of released but intact nucleic acid molecules can be very low. Because of the potential for destruction of the product, the standard disruption methods must all be reevaluated when the product molecule is DNA or RNA, particularly when it is necessary to recover intact plasmid DNA.

We evaluated five different mechanical disruption processes to determine their potential as cell disruption methods for DNA (plasmid) products. A model host-plasmid system was grown for cell paste. The cell paste was isolated then resuspended in a TE disruption buffer and the suspension was processed through different bench or pilot scale cell disruption equipment under conditions suggested by the manufacturers, reported in publications, as well as developed by the inventor of this patent. The intact cells and cell debris were separated from soluble molecules by high speed centrifugation in microfuge tubes, and the amount of intact plasmid DNA remaining in the cells, released into the liquid phase, and destroyed in the disruption process were measured by quantitative gel electrophoresis with the aid of image analysis equipment. The findings show that most common disruption methods result in almost complete destruction of released plasmid DNA and consequently very low plasmid yields. However, two methods appear to be relatively mild in terms of shearing the plasmids and could be used for high yield recovery of intact plasmid from bacterial cells, preferably E. coli.

One embodiment of the invention relates to a mechanical method for disruption of plasmid-containing bacterial cells and release of intact plasmid DNA which can then be isolated. The method comprises the steps of first passing liquid suspension of plasmid-containing bacterial cells between one and three times through an impinging-jet homogenizer with a single interaction chamber at an operating pressure of about 750 to 4,000 psi, preferably about 1,000 to 3,000 psi, more preferably about 2,000 psi, whereby the bacterial cells are disrupted and intact plasmid DNA is released. The disrupted bacterial cell debris is then separated from the liquid containing intact plasmid DNA. The plasmid may then be further isolated and purified. Another embodiment of the invention relates to a mechanical method for disruption of plasmid-containing bacterial cells and release of intact plasmid DNA. The method comprises the steps of first passing liquid containing plasmid-containing bacterial cells through a bead mill containing beads of about 0.1 mm to about 1 mm in diameter, at an agitation speed of about 1,000 to 2,500 rpm. Because, such lower-speed agitation disrupts cells with minimal damage to plasmid contained therein, either batch mode, single-pass processing or multiple pass processing can be used so long as the total processing times are similar. With multiple pass processing, the liquid is passed through the bead mill at least two times, preferably four to eight times, more preferably between five and six times, for a residence time in the bead mill of about 0.5 to about 3 minutes per pass, whereby bacterial cells are disrupted and intact plasmid DNA is released. If a single batch mode, using a single pass operation is used, the liquid suspension of plasmid-containing bacterial cells is processed in the bead mill for at least three minutes, preferably between about five and thirty five minutes, more preferably between about ten and twenty minutes, whereby bacterial cells are disrupted and intact plasmid DNA is released. The disrupted bacterial cell debris is then separated from the liquid containing intact plasmid DNA. The plasmid may then be further isolated and purified.

DETAILED DESCRIPTION OF THE INVENTION

Figure 1:
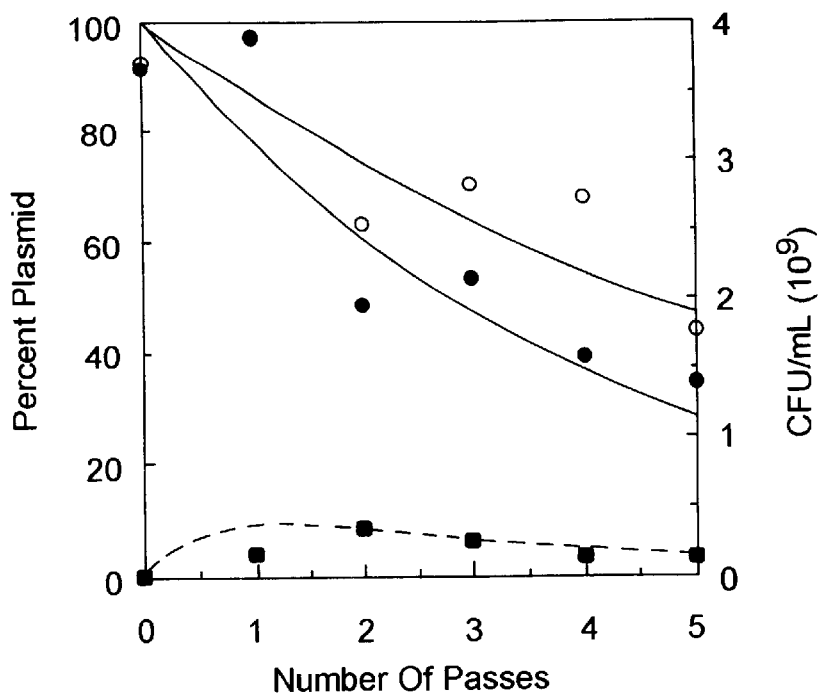
FIG. 1. Results with MICROFLUIDIZER® jet impingement device operated at 500 psi with an HC-5000 (low pressure) device. ○ cell viability, ● DNA remaining associated with cells in pellet. ■ soluble DNA. The solid lines are for a first order disruption model with rate constants of 0.25 and 0.15 per pass. The dashed line is for a reaction-in-series model with disruption rate constant of 0.25 per pass and destruction rate constant of 2.0 per pass.

The invention relates to mechanical methods for disruption of bacterial cells for release of intact plasmid DNA from bacteria, preferably E. coli, in particular, recovery of intact plasmnid DNA from bacteria transfected with a recombinant plasmid capable of expressing a heterologous nucleic acid sequence of interest. In one such method a liquid suspension, plasmid-containing bacteria passes between one and three times, preferably one time, through an impinging-jet homogenizer, preferably a MICROFLUIDIZER® impinging-jet homogenizer, at an operating pressure of about 750 to 4,000 psi, preferably about 1,000–3,000 psi, more preferably about 2,000 psi, whereby bacterial cells are disrupted and intact plasmid DNA is released; the bacterial cell debris is then separated from the supernatant containing intact plasmid DNA. In another such method liquid suspension containing plasmid-containing bacteria is processed through a bead mill containing beads about 0.1 to about 1 mm in diameter, preferably about 0.25 to about 0.75 mm, more preferably about 0.5 mm in diameter; at an agitation speed of about 1,000 to 2,500 rpm, preferably about 2,000 rpm; and wherein the liquid is processed through the bead mill either (1) in a single-pass mode for a residence time of at least three minutes, preferably about five to thirty five minutes, more preferably about ten to twenty minutes, or (2) in a multiple-pass mode for at least two passes, preferably between four (4) and eight (8) passes, more preferably five (5) to six (6) passes, for a residence time in the bead mill of about 0.5 to about 3 minutes per pass, preferably about 2 minutes per pass, whereby bacterial cells are disrupted and intact plasmid DNA is released; the bacterial cell debris is then separated from the liquid containing intact plasmid DNA; intact plasmid DNA may then be isolated. Preferred for mechanical disruption according to the methods of the invention are bacterial cells, preferably E. coli bacterial cells.

Once the cells have been mechanically disrupted and the liquid that contains intact plasmid is separated from cellular debris, the intact plasmid may undergo further isolation and purification. Methods of additional purification and isolation include, but are not limited to, column chromatography, gel electrophoresis isolation and dialysis, and gradient centrifugation.

The methods of the invention are suitable for mechanical disruption of the cells of a variety of bacteria, including E. coli, Bacillus species including Bacillus subtilis, and Streptonzyces sp. E. coli is preferred.

Plasmids which can be isolated from cells by the methods of the present invention include commercially available expression vectors which can be used in well known recombinant DNA expression systems. Plasmids are commercially available from a variety of suppliers such as, for example, Invitrogen (San Diego, Calif.), Stratagene (San Diego, Calif.), New England BioLabs Co. (Mass.), ProMega Co., and BRL, Inc. The product catalogs, which are incorporated herein by reference, of each of these companies describe plasmids useful in the methods of the present invention. Commercially available plasmids may used as starting material to produce desired gene constructs which include coding sequences of desired expression product operably inserted into expression sites of the plasmid.

Methods

Cell Paste Preparation

E. coli strain DH5α (Gibco BRL, Life Technologies, Inc., Gaithersburg, Md.) containing 10.4 kb plasmid pCEP4 (Invitrogen Corp., San Diego, Calif.) was cultured using standard protocols in 30 L or 80 L New Brunswick reactors (MPPF-80L, New Brunswick Scientific, New Brunswick, N.J.) using a media containing Ardamine Z yeast extract (Champlain, Inc., Clifton, N.J.) (24 g/L), Soytone SF (Staley, Inc. Protein Division, Decatur, Ill.) (12 g/L), and 2% w/v glucose. After growth, the culture broth was centrifuged in a SHARPLES® centrifuge (Model AS16Y, Alfa-Laval Separation, Inc., Warminster, Pa.) at approximately 16,000 rpm with a throughput flowrate of approximately 1.5 L/min to collect cell paste.

Cell Paste Storage

The cell paste was either used immediately (same day) or was stored at −70° C. in a Queue ultra-low freezer. Samples were thawed minimally for resuspension and disruption experiments.

Alkaline Lysis Method

Plasmids were prepared for electrophoresis using a variation of the alkaline lysis method originally presented by Bimboim and Doly (1979) as modified in *Current Protocols in Molecular Biology*, Vol. 1, Chap. 1, Ed. Ausubel et al., Pubs. Greene/Wiley & Sons (1993). In a typical preparation, 100 μL of sample (either centrifuged in a microcentrifuge, Model MVSS (Costar Inc, Cambridge, Mass) at 10,000 rpm (supemate) or not (unspun) was added to a polypropylene Eppendorf test tube and 200 μL of 0.2 N NaOH/1%SDS was added. The solution was mixed then put on ice for five to ten min. 150 μL of KOAc was added, the solution mixed and placed on ice for five to ten minutes. The suspension was then centrifuged for three to four minutes, and 425 μL of the supemate was transferred to a fresh Eppendorf test tube. 850 μL of 100% EtOH was added, the solution was mixed, and the resulting suspension was allowed to precipitate for 1 hour. The suspension was then centrifuged for five minutes, the supernate was removed and discarded, and the pellet was rinsed in 70% EtOH. The suspension was recentrifuged, then dried using a Speed-Vac. Finally the pellet was dissolved in 20–25 μL of TE buffer (50 mM Tris-20 mM EDTA). Recovery of intact plasmid DNA using this alkaline lysis procedure was then compared, using the methods described below, to recovery of intact plasmid DNA using the various mechanical cell disruption methods.

HindIII Digestion

HindIII from Boeringer Mannheim (10 μLg/,uL) was used to digest the plasmid DNA to the linear form. To 5 μL of DNA solution was added 1 μL of 10x buffer, 0.5 μL of HindIII solution and 3.5 μL of dH$_2$O in an Eppendorf test tube. The mixture was incubated at 37° C. for (at least) one hour. Just before loading the solution on the gel, 2 μL of 6x loading buffer/dye and 0.5 μL of 1 mg/mL RNase solution was added to the sample.

Agarose Gel Electrophoresis

Agarose gel electrophoresis was conducted using a model MPH unit from International Biotechnologies, Inc. (New Haven, Conn.). Eight-tenths (0.8) g of agarose were added to 100 mL of tris-borate-EDTA (TBE) buffer and the mixture was heated to boiling in a microwave (~2 minutes—stop after 1.5 minutes, swirl, heat 20–30 sec, swirl until agarose is dissolved). Six (6) μL of 10 mg/mL ethidium bromide was added and the gel solution was cooled to 60–70° C. by running warm tapwater over the flask containing the agarose solution. The solution was then poured into a tray mold with comb in place. After polymerization (~20 min) the comb was removed, and the gel was covered with TBE buffer in the electrophoresis chamber. 25 μL of EtBr solution was added to the buffer and the solution was mixed. Ten (10) μL of each sample was added to the wells, and the system was then run for 4 hrs at 100 V.

λ DNA marker from International Biotechnologies, Inc. (New Haven, Conn.) was used as a size standard. Three (3) μL of HindIII cut λ DNA (0.240 μg/μL) was mixed with 7 μL of TE buffer. The mixture was heated to 70° C. for 4 minutes, then cooled on ice. Two (2) μL of dye solution was added, then 10 μL of the mixture was loaded on the gel.

Gel Quantification

Gel quantification was done by image analysis using the NIH image analysis program version 1.47 (National Institutes of Health, Bethesda, Md.) on a MacIntosh computer. A camera image of a fluorescing gel was captured on disk by use of a high resolution video camera with a UV filter coupled to an image digitizer (Foto/Analyst Visionary Model 2200 Fotodyne Inc., New Berlin, Wis.). The lanes were scanned for band intensity corresponding to peak areas via calculation from the program. The areas of the peaks were compared to standards to determine the amount of plasmid in each lane.

Cell Viability Determination

Cell viability was determined from quantitative agar plate counts. Plating was accomplished using a Model DU type automatic spiral plater (Spiral Systems, Cincinnati, Ohio). Raw samples were diluted with sterile PBS at pH 7.4 to $10^{-5}$, $10^{-6}$, or $10^{-7}$ depending on the optical density of the original sample. The diluted samples were then plated out with the device onto LB-agar (15 g/L) plates or LB-agar containing 100 μg/mL ampicillin (Amp+). The plates were incubated for 15 hours at 37° C.; colonies were counted according to the plater manufacturer's instructions.

Optical Inspection

Cell suspensions were optically inspected to determine the fraction of intact cells remaining after disruption procedures. Samples of control and disrupted cell suspensions were examined under a Nikon compound microscope using oil immersion @ 1000xphase contrast magnification.

Optical Density

The optical densities of the cell suspensions were determined using a Perkin-Elmer Lamda 2 UV/V is spectrometer at a wavelength of 600 nm. Solutions were diluted with TE buffer so that readings were in the range 0.1–0.8 OD units.

Mechanical Cell Disruption Methods

Sonication

Sonication was carried out on an XL2020 sonicator (Heat Systems Inc., Farmingdale, N.Y.) using the microtip attachment. One (1) mL samples were sonicated for prescribed amounts of time in 1.5 mL Eppendorf microfuge tubes in a freezing test tube rack (to maintain samples at cool temperatures).

Nebulization

A BIONEB™ Nebulizer (Glas-Col, Terre Haute, Ind.) was used as per the manufacturer's instructions at 50, 85, or 175 psi with nitrogen gas using either the once-through method with multiple passes or the recycling mode.

Gaulin Mill

Processing with a Gaulin homogenizer, Type 15M8TA, (APV Gaulin, Inc., Everett, Mass.) was conducted at 3000, 5000, or 7000 psi for from 1 to 3 passes at each pressure. A standard knife was used in the device.

MICROFLUIDIZER® Impinging Jet Homogenizer

For microfluidization processing cells were processed using either a model HC-5000 (low pressure<2000 psi) or Model M-110Y (high pressure>2000 psi) MICROFLUIDIZER® homogenizer, (Microfluidics, Inc., Newton, Mass.). The F20Y interaction chamber was used with the Model M-110Y device, as were H210Z and H230Z interaction chambers. A J20Y interaction chamber was used with the low pressure device (HC-5000).

DYNO®MILL Bead Mill

A type KDL pilot scale bead mill from Glen Mills Inc., Clifton, N.J., was used for bead mill experiments. The cell suspension was pumped at high (695 mL/min) or low (303 mL/min) flow rate with a Masterflex peristaltic pump. The bead chamber was filled with approximately 1170 cc of 0.5 mm dry glass beads (chamber volume is 1.4 L). Agitation was either at low speed (1910 rpm) or high speed (3400 rpm).

Modeling

In order to condense the results from various experiments into parameter estimates, a first-order reaction in series model was used to represent the release-destruction reactions involved in DNA liberation from the cells. The cell disruption process was considered to be a first order process in accordance with previous modeling efforts for the bead mill, homogenizer and microfluidizer. A qualitative fit to the observed cell disruption data was made to estimate the "rate constant" for cell disruption. Where appropriate data were available, the rate constant for the second reaction, DNA destruction, was obtained by a simple trial and error fitting to observed data. No attempt was made to relate values of either parameter to more fundamental fluid dynamics involved in the process.

Results

Sonicadon

Ultrasonic cell disruption occurs when sound waves having a frequency in the order of about 20,000 cps (20 kHz) are converted to very rapid vibration in a liquid, thereby producing a phenomenon called "cavitation". Cavitation occurs when the rapid vibration produces low pressure areas within the liquid. Gas bubbles may form in areas where the pressure drops below the vapor pressure of the liquid. However, these bubbles collapse when local pressure rises again, sending a shock wave and creating shear forces through the liquid which will disrupt cells. The sound waves are directed into the liquid through a "sonicator" tip or "horn". The use of sonication for large scale cell disruption is reported to be limited by the output that is possible from a sonicator tip as well as the large amount of heat generated. (Wheelwright, S. M., *Protein Purification:Design and Scale up of Downstream Processing*, Oxford University Press (1991), in Chapter 6: Cell Disruption, at page 64.)

In a first set of experiments a cell suspension was processed for from 0 to 5 minutes at 50% duty setting and 50% maximum power input. According to other publications, such as (2 minutes at these processing intensities is normally sufficient in the laboratory to produce cell disruption of over 90% of the cells and, for practical purposes, intracellular β-galactosidase such as protein is released completely in this process, depending on the length of time the suspension is processed. After about 2 minutes the activity of released β-galactosidase decreases with further increases in the processing time).

After 30 seconds of processing, the cell debris was removed by high speed centrifugation and the resulting supernatant subjected to agarose gel electrophoresis as described above. There were no plasmid bands in the gel lanes at the position corresponding to intact released plasmid. After alkaline lysis of uncentrifuged sample (containing intact cells and cell debris), faint but distinct plasmid associated bands representing both released and unreleased plasmid were sometimes seen. This was interpreted as that the plasmid remaining in the undisrupted cells was the only plasmid still intact. Similar results were obtained with longer processing times, but the amount of DNA seen in the uncentrifuged lanes decreased as the process time increased. This is consistent with the idea that as more cells were disrupted, more DNA was destroyed by the process. Little or no intact DNA corresponding to the supernate fraction was ever obtained.

A second experiment was run to explore this behavior further. Plasmid DNA was isolated from cells using a large scale alkaline lysis procedure. The purified plasmid DNA isolated in this way was resuspended and the solution was processed with the sonication horn for 30 seconds. The sonicate was reprecipitated, resuspended in a smaller volume and run out on a gel. The gel showed that there was little or no intact DNA after sonication.

From these two experiments, it is clear that sonication produced cell disruption but little or no intact plasmid. The plasmid released from cells were substantially and rapidly destroyed by sonication.

Nebulization

A BIONEB nebulizer was used to disrupt cells according to the manufacturer's instructions. Different nozzle pressures, processing times, and recycle configurations were tested.

The nebulizer effectively disrupted cells as determined by the amount of intra cellular plasmid DNA remaining intact in cell suspensions vs the corresponding centrifugate. In the batch mode, the percent of the original plasmid associated with intact cells decreased as the number of passes through the equipment increased. Higher pressures at the disruption nozzle also increased the amount of cell disruption. After 1 pass at 175 psi, about 40% of the original plasmid was identified as associated with intact cells (i.e., unreleased). This decreased to around 16% after 3 passes at this pressure. Similar results were seen at 85 psi and 50 psi. After 1 pass about 40% of the cells were disrupted at both pressures. After 3 passes the disruption was around 60 and 40% respectively.

The DNA recovery from the nebulizer was low in all cases. The maximum amount of intact DNA found in the supernate was 12% of the original DNA. After 3 passes 80% of the original plasmid DNA was destroyed at 175 psi. At 85 and 50 psi the amount destroyed was estimated from gels to be around 50% and 30% respectively.

A very similar result was obtained when the nebulizer was operated in the recycle mode, except that the amount of recovered plasmid DNA was even lower. A maximum of about 3% of the original DNA was obtained in the supernate in this mode. Cell disruption increased from about 50–70% after 1 minute of processing to 70–90% after 5 minutes of processing. Almost no intact plasmid DNA was found in the supernate after 5 minutes of processing.

Gaulin Mill (Homogenization)

The high pressure Manton-Gaulin APV homogenizer is widely used for cell disruption when recovery of protein product is the goal. It consists of a positive displacement pump with one or more pistons connected to a special nozzle. On the pressure stroke, the cell suspension is forced through an adjustable restricted orifice (homogenization valve). With a CD (cell disruption) valve and modified pump design the machine is called a CD homogenizer. The CD homogenizer was designed specifically for applications in the field of biotechnology and genetic engineering, where intracellular proteins and enzymes need to be released from the interior of the cell prior to recovery.

Disruption is believed to occur through a variety of mechanisms, including shear, cavitation, and impingement. Sauer, Robinson and Glick, supra, at page 1330–1331, review prior reports of Gaulin mill disruption of yeast and $E.$ $coli$. In general, the degree of disruption has been reported to be proportional to the number of passes and the operating pressure, and first order disruption kinetics were observed for isolation of intracellular protein and beta-galactosidase from $E.$ $coli$.

The following experiment demonstrated that the Gaulin Mill to be effective for cell disruption. At a pressure drop of 3000 psi (low) around 10% of the cells were disrupted after 1 pass (as determined by visual inspection and counting in a Petroff-Houser cell). This increased to around 20% after 3 passes through the device. At medium pressure (5000 psi) disruption was higher, around 25% after one pass up to 75% after 3 passes. At high pressure (7000 psi) the values were around 70% after one pass and 90% after 3 passes. Similar values were obtained from viable cell plate counts.

DNA recovery was better than with the Nebulizer or sonicator, but still not high enough. Qualitative inspection of gels from supernate and uncentrifuged suspensions indicate that up to 30% of the original plasmid could be recovered in the supernate under the best processing conditions, i.e., at 5000 or 7000 psi and one pass through the device. Multiple passes appeared to destroy significant amounts of released DNA.

MICROFLUIDIZER® Impinging Jet Homogenizer

The MICROFLUIDIZER® homogenizer, (Microfluidics Corp., Newton, Mass.), is an impinging-jet fluidizer or homogenizer, a type of high-pressure homogenizer (See U.S. Pat. No. 4,533,254) wherein a pressurized fluid stream diverges into a plurality of flow paths which subsequently re-converge so that the flows are impinged upon each other at high velocity against a stationary surface in an interaction chamber. High pressure and the fixed geometry of the interaction chamber provide shear, impact and cavitation forces. All product passes through the interaction chamber and all product is subjected to uniform process conditions. Wheelwright, S. M., *Protein Putification:Design and Scale up of Downstream Processing*, Oxford University Press (1991), in Chapter 6: Cell Disruption, at page 66, teaches that operating pressures for cell disruption with the impinging jet fluidizer are 35–70 MPa (5,000 to 10,000 psi) (conversion: 0.1 MPa=100 Kp=1 bar=14.5 psi). Agerkvist and Enfors, supra at 1089 teach that one pass through the MICROFLUIDIZER impinging-jet homogenizer degrades the cellular DNA polymer to smaller fragments. This is desirable where protein recovery is the goal in that it decreases the viscosity of the solution and facilitates subsequent removal of cellular debris through filtration; it suggests, however, that cell disruption with the impinging-jet homogenizer may not be feasible where the goal is to recover intact plasmid DNA.

The following experiments tested the ability of the microfluidizer to disrupt cells and release intact plasmid DNA at conditions very different from recovery proteins. Initial experiments were carried out using 2 interaction chambers in series. The results were not satisfactory. Based on the results of preliminary tests, the operating conditions and two types of processing systems were selected for the experiments using the microfluidizer with a single chamber. The first set of experiments used a low pressure system, covering the range of 500 to 2000 psi at the processing rates used here. The other set of experiments a high pressure system and covered the range of 2000 to 4500 psi.

Figure 2:
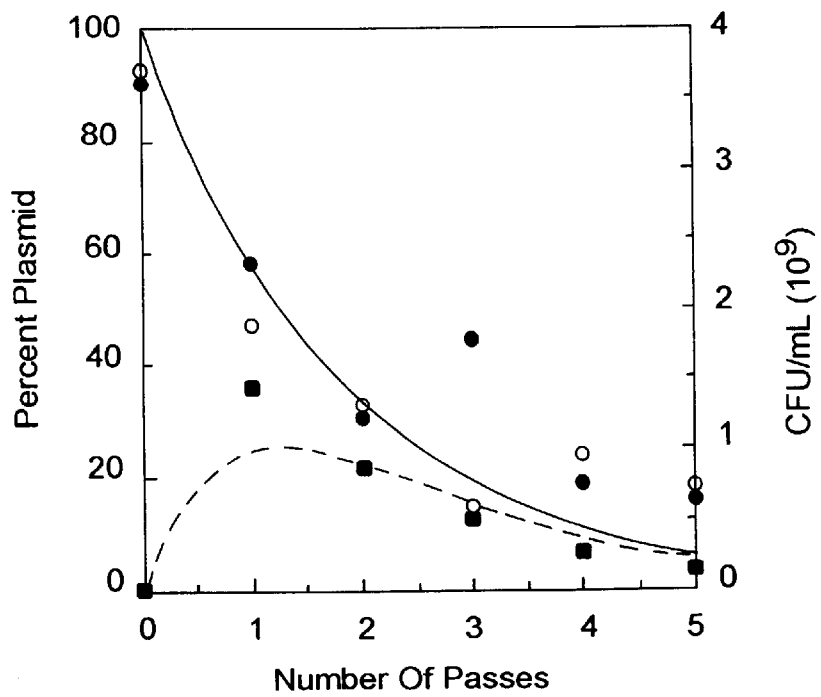
FIG. 2. Results with MICROFLUIDIZER® jet impingement device operated at 1000 psi with an HC-5000 (low pressure) device. ○ cell viability, ● DNA remaining associated with cells in pellet. ■ soluble DNA. The solid line is for a first order disruption model with a rate constant of 0.55 per pass. The dashed line is for a reaction-in-series model with a disruption rate constant of 0.55 per pass and DNA destruction rate constant of 1.1 per pass.
Figure 3:
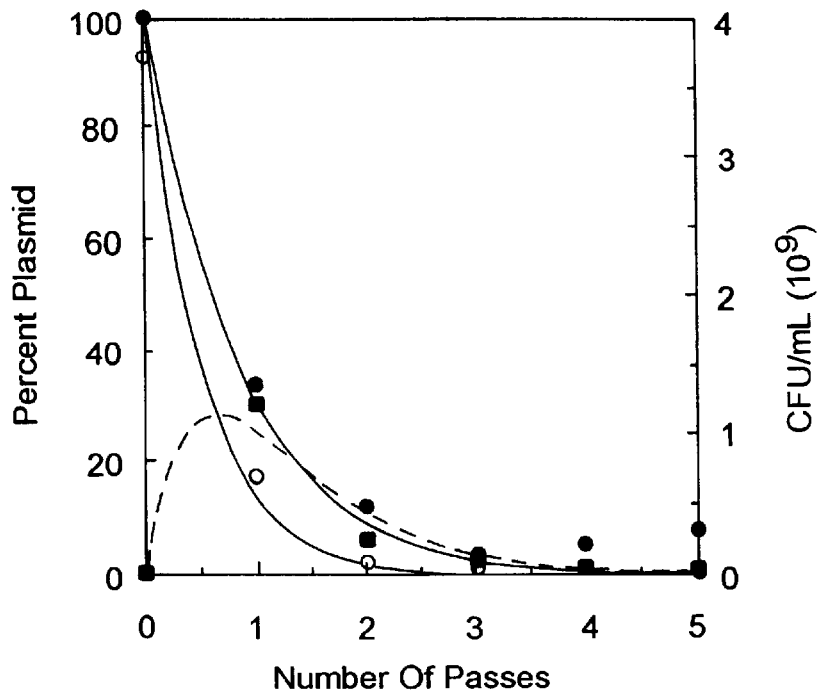
FIG. 3. Results with MICROFLUIDIZER® jet impingement device operated at 2000 psi with an HC-5000 (low pressure) device. ○ cell viability, ● DNA remaining associated with cells in pellet. ■ soluble DNA. The solid lines are for a first order disruption model with rate constants of 2.0 and 1.2 per pass. The dashed line is for a reaction-in-series model with disruption rate constant of 1.2 per pass and DNA destruction rate constant of 2.0 per pass.

Cell disruption in the low pressure arrangement resulted in increasing rates of cell disruption (per pass) as the processing pressure was increased (See FIGS. 1–3). At 500 psi, around 40% of the cells were disrupted after 2 passes, and 60% were disrupted by 5 passes. At 1000 psi the values were around 70% and 85% after the same number of passes respectively. At 2000 psi over 90% and nearly 100% of the cells were disrupted after 2 and 5 passes respectively. The fraction disrupted as determined by viability counts was similar to that determined by DNA release.

Figure 4:
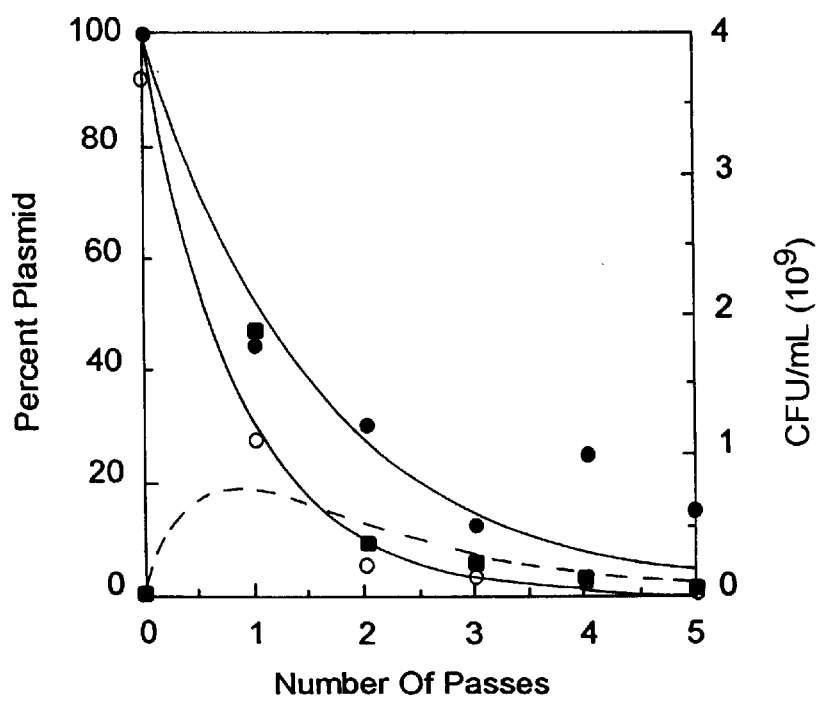
FIG. 4. Results with MICROFLUIDIZER® jet impingement device operated at 2000 psi with an MY-110Y (high pressure) device. ○ cell viability, ● DNA remaining associated with cells in pellet. ■ soluble DNA. The solid lines are for first order disruption model with rate constants of 1.2 and 0.65 per pass. The dashed line is for a reaction-in-series model with disruption rate constant of 0.65 per pass and DNA destruction rate constant of 2.0 per pass.
Figure 5:
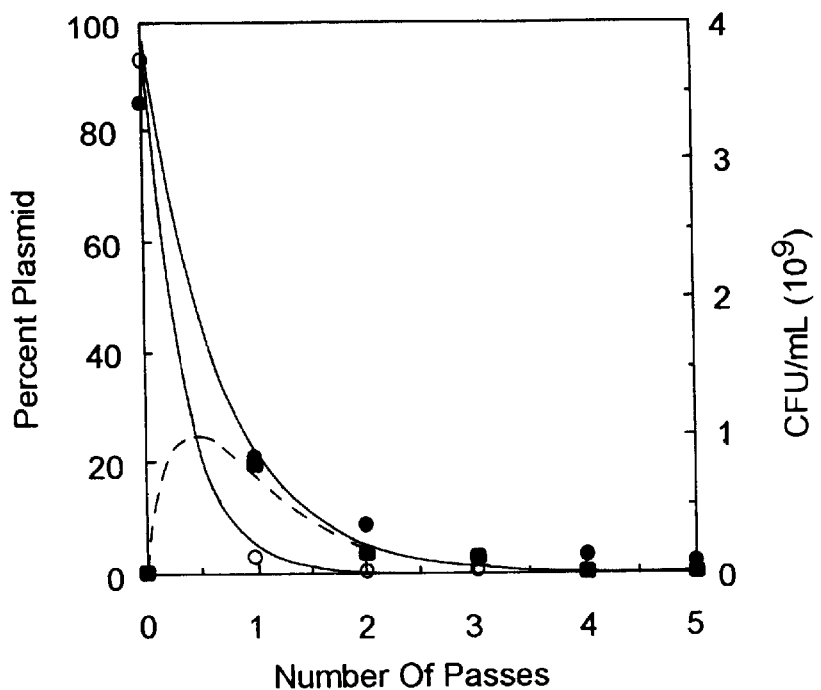
FIG. 5. Results with MICROFLUIDIZERO® jet impingement device operated at 4500 psi with an MY-110Y (high pressure) device. ○ cell viability, ● DNA remaining associated with cell in pellet. ■ soluble DNA. The solid lines are for a first-order disruption model with rate constants of 3.0 and 1.5 per pass. The dashed line is for a reaction-in-series model with disruption rate constant of 1.5 per pass and DNA destruction rate constant of 3.0 per pass.

Using the high pressure system, disruption, as determined by viable cell counts, was around 75% after 1 pass at 2000 psi, and nearly complete by 5 passes (FIG. 4). Slightly lower values for released plasmid (55% and 85%) were obtained from gel estimates. At 4500 psi cell disruption was nearly complete even after 1 pass according to viable cell counts and 80% complete according to gel estimates based on the DNA recovery (FIG. 5).

At 500 psi with the low pressure system, the maximum amount of plasmid DNA recovered in the supernate fraction was around 10% after any number of passes through the device. At this maximum, around 30% of the DNA was destroyed in the disruption process. Higher DNA recoveries were observed with the low pressure system at 1000 psi. About one-third (35%) of the original plasmid DNA was found in the supernate after one pass, this corresponding to only around 5 to 10% destruction of the DNA. More passes resulted in less intact plasmid DNA in the supernate, due to higher destruction. Nearly all (>90%) of the DNA was destroyed after 5 passes.

At 2000 psi the results were similar to those at 1000 psi, the maximum DNA recovery in the supernate was around 30% after 1 pass, however this corresponded to about 40% destruction. All of the DNA was destroyed by 5 passes.

Using the high pressure system, similar results were obtained at 2000 psi (FIG. 4). The maximum amount of soluble plasmid DNA was 50% of the original plasmid DNA after 1 pass, this corresponded to only 10% destruction of the plasmid DNA in the process. Repeated passes lowered the amount of plasmid DNA in the supernate and raised the amount destroyed. At higher pressure (4500 psi) the amount of DNA recovered after 1 pass was only 20% and this represented about 60% destruction of the DNA.

DYNOMILL® (Beadmill)

A bead mill is a mechanical grinder which has a chamber filled with a grinding medium such as glass beads. The cell suspension placed in the chamber, where a turning shaft causes the beads to impact against the cells, disrupting them. There may be discs spaced along the shaft. Alternatively, the grinder may have a rolling or vibrating chamber which throws the beads against the sides, thereby disrupting the cells. Cell disruption in mechanical grinders results from the impact and shear force of the grinding medium against the cells.

Glass beads are a typical medium for grinding cells, although ceramic or stainless steel beads are also used. Bacteria typically require smaller beads, typically about 0.1 mm diameter, while yeast cells require slightly larger beads, about 0.5 mm in diameter. Both the nature of the grinding medium and the shaft speed, or peripheral velocity, are important parameters affecting the results obtained. Other factors affecting the rate of disruption and the fineness of the particles generated are the throughput or flow rate, the viscosity, the temperature, the configuration of the grinder (e.g., spacing between discs on the shaft), and the ratio of grinding medium to total volume. (See Wheelwright supra, at 67–70.)

The DYNO®MILL KDL pilot scale bead mill is used to effect cell disruption. The cell suspension is pumped through a horizontal grinding chamber filled to about 80 to 85% with microspheres (beads). A shaft fitted with discs agitates the beads and the impact and shearing forces of the beads against the cells produces cell disruption without damaging intracellular proteins, enzymes, or other cellular components.

Figure 6:
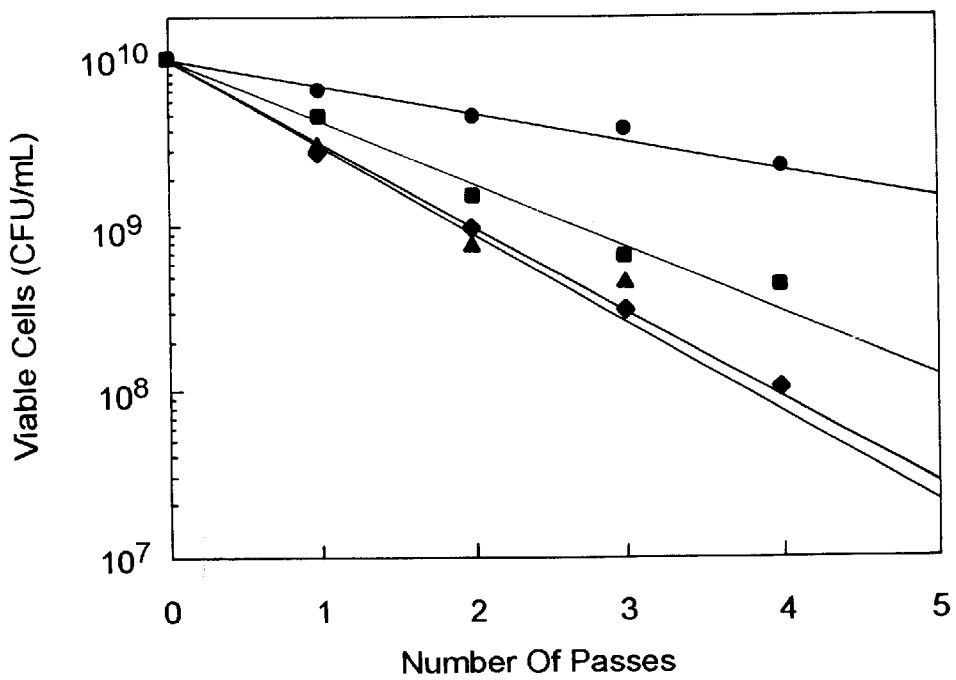
FIG. 6. Summary of cell disruption kinetics, based on viability, with the KDL pilot bead mill based on first order model. ■ low speed (1910 rpm), high flow (695 mL/min); k=0.9 per pass. ▲ Low speed (1910 rpm), low flow (303 mL/min); k=1.25 per pass. ◊ High speed (3400 rpm), low flow (303 mL/min); k=1.2 per pass. ○ High speed (3400 rpm), high flow (695 mL/mnin); k=0.4 per pass.
Figure 7:
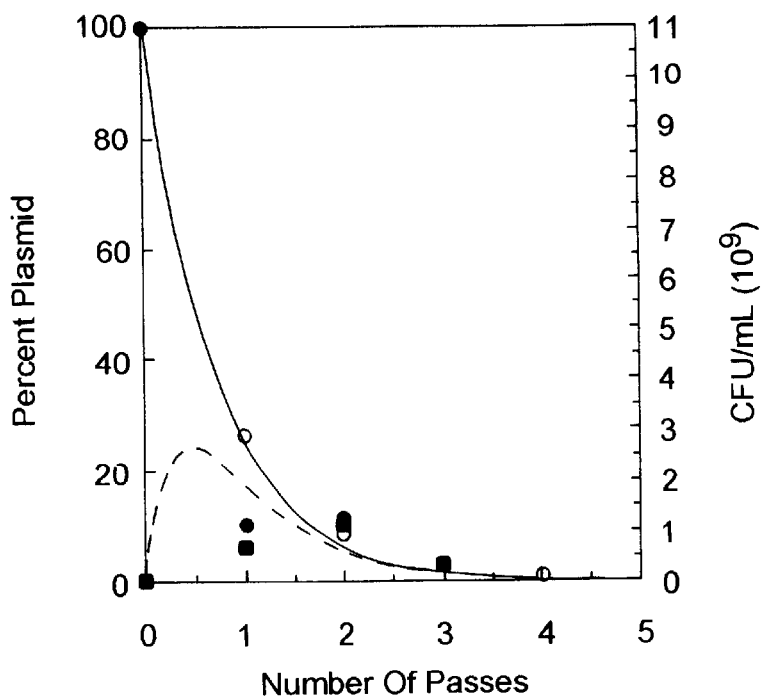
FIG. 7. Bead mill results operated at high agitation speed (3400 rpm) and low flow rate (303 Ml/min). ○ cell viability, ● plasmid remaining in cells, ■ soluble plasmid. The solid line is for a first-order model of disruption with a rate constant 1.4 per pass. The broken line is the intermediate product of a first order reaction-in-series model with disruption rate constant of 1.4 per pass and DNA destruction rate constant of 3.0 per pass.
Figure 8:
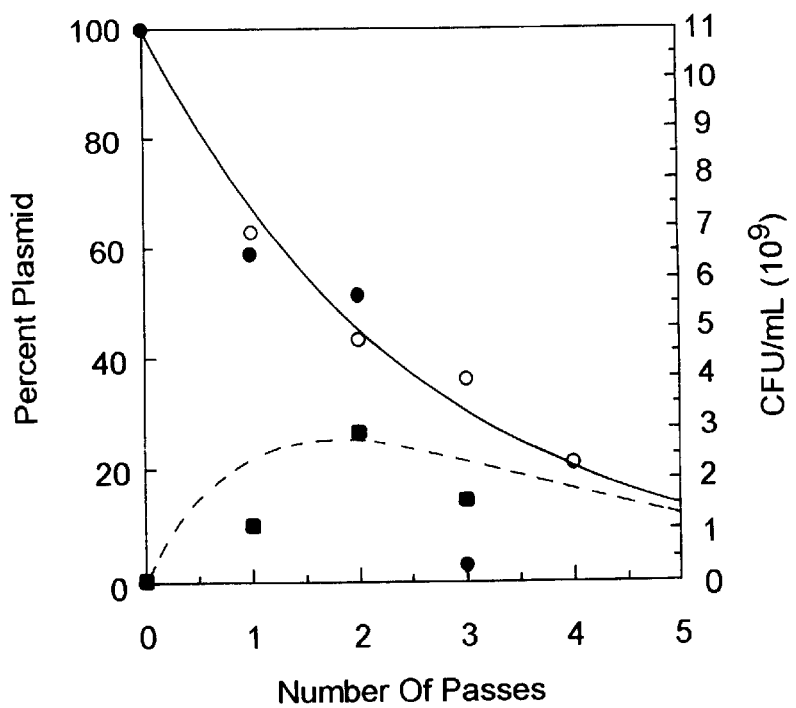
FIG. 8. Bead mill results operated at high agitation speed (3400 rpm) and high flow rate (695 Ml/min). ○ cell viability, ● plasmid remaining in cells, ■ soluble plasmid. The solid line is for a first order model of disruption with a rate constant 0.4 per pass. The broken line is the intermediate product of a first order reaction-in-series model with disruption rate constant of 0.4 per pass and DNA destruction rate constant of 0.8 per pass.
Figure 9:
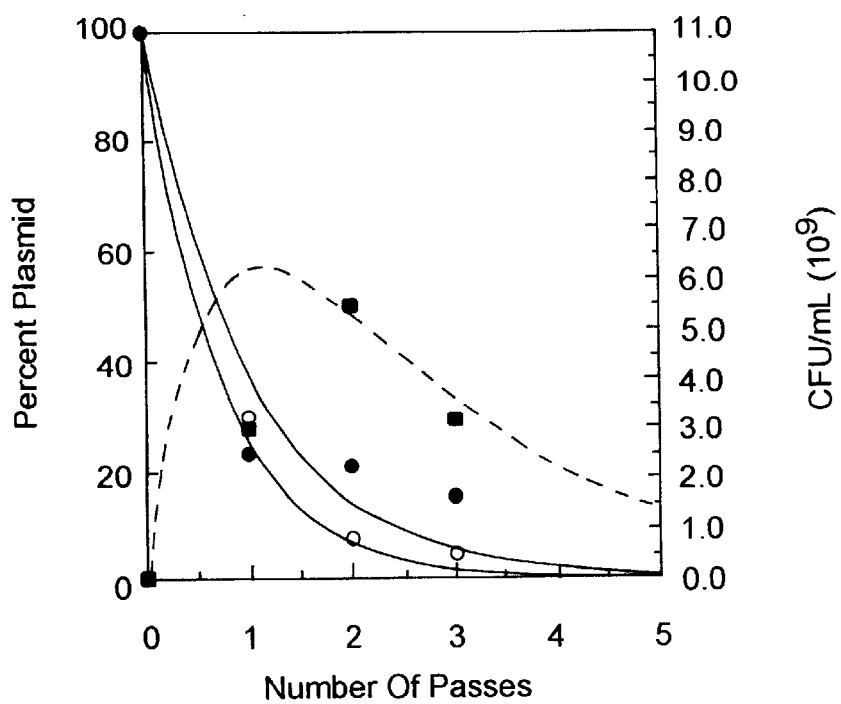
FIG. 9. Bead mill results operated at low agitation speed (1910 rpm) and low rate (303 Ml/min). ○ cell viability, ● plasmid remaining in cells, ■ soluble plasmid. The solid lines are for a first order model of disruption with rate constants of 1.4 and 1.0 per pass. The broken line is the intermediate product of a first order reaction-in-series model with disruption rate constant of 1.4 per pass and DNA destruction rate constant of 0.5 per pass.
Figure 10:
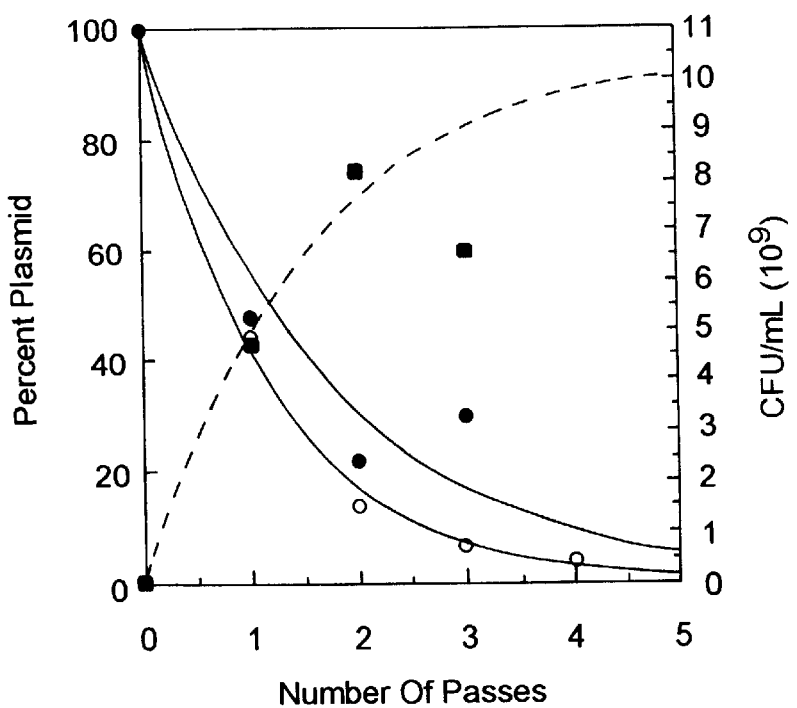
FIG. 10. Bead mill results operated at low speed (1910 rpm) and high flow rate (695 Ml/min). ○ cell viability, ● plasmid remaining in cells, ■ soluble plasmid. The solid lines are for a first order model of disruption with a rate constants of 0.9 and 0.6 per pass. The broken line is the intermediate product of a first order reaction-in-series model with disruption rate constant of 0.6 per pass and DNA destruction rate constant of 0.01 per pass.

The bead mill effectively disrupted cells under all conditions tested. Two feed rates, 303 and 695 ml/min, and two agitation speeds, 1910 and 3400 rpm were used in four unique experiments. Cell disruption was most complete under low flow (high residence time) and high agitation speeds; 70–90% of the cells were disrupted in a single pass at this condition. The fraction disrupted after 4 passes was greater than 95%. Cell disruption was least complete at the low speed-high flow condition. Only around 50% of the cells were disrupted after a single pass at this condition. The low speed-low flow and high speed-high flow conditions followed suit, the former being slightly more destructive to the cells than the latter. The results are summarized in FIG. 6.

FIGS. 7–10 show the plasmid DNA recovery for each of the conditions. At high speed with a low flow rate (FIG. 7) a maximum of about 10% of the original plasmid DNA was recovered in the supernate. This corresponded to about a 12% recovery of the released plasmid DNA. At high speed with a high flow rate (FIG. 8) about 25% of the total plasmid DNA was found in the supernate after 2 passes, corresponding to about a 33% recovery of the released plasmid DNA. These values dropped to 12 and 15% after 3 passes.

At low speed with a low flow rate (FIG. 9) up to 50% of the plasmid DNA was found in the supernate after 2 passes through the bead mill. This corresponded to about 60% of the released plasmid DNA. Another pass resulted in only about 30% of the plasmid DNA in the supernate, still representing about a 60% recovery of released plasmid DNA. At low speed with a high flow rate (FIG. 10) 60 to 80% of the original plasmid DNA was released from the cells after several passes. The soluble intact plasmid DNA represented up to 95% of the DNA actually released from the cells.

Figure 11:
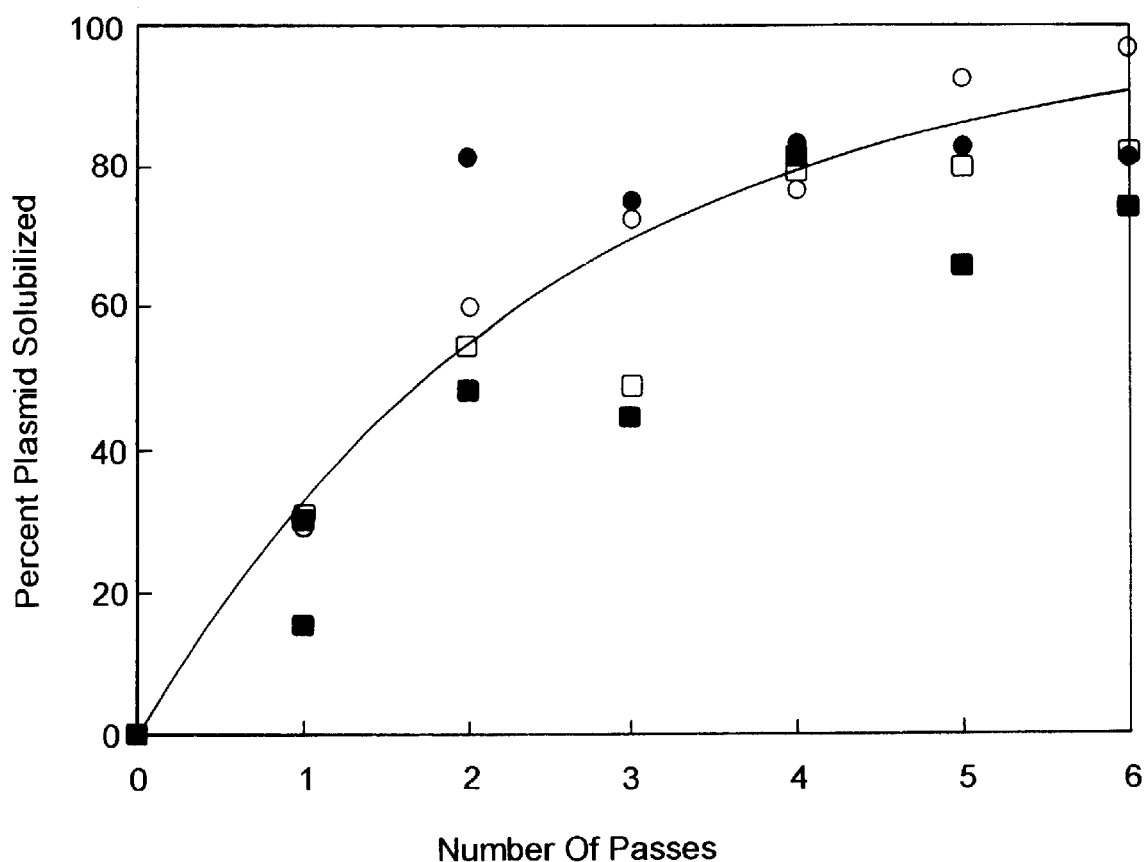
FIG. 11. Bead mill results operated at low agitation speed (1910 rpm) and low flow rate (695 mL/min.) ○ fresh cells at a starting OD of 200 AU. ● frozen cells at a starting OD of 200 AU. □ fresh cells at a starting OD of 40 AU. ■ frozen cells at a starting OD of 40 AU. The curve is for a reaction-in-series model with a cell disruption rate constant, $k_c$, of 0.4 per pass and a plasmid degradation rate constant, $k_p$, of 0.01 per pass.

The low agitation speed, high flow rate (i.e., low residence time) processing conditions were repeated with other samples of frozen and fresh cells resuspended to optical densities of 400 AU or 200 AU at 600 nm (AU). The results are shown in FIG. 11. Under these conditions disruption of cells appeared most complete in the higher density suspension. Over 95% of the plasmid originally in the cells was found as soluble plasmid after six passes through the mill. Fresh and frozen cells appeared to give similar results. Similarly, there was substantial release of intact plasmid in the low density (AU=40) suspensions; about 80% of the original plasmid was found intact in the solution phase after six passes. Although processing of the higher density suspension was more efficient, comparable plasmid recovery is probably attainable with lower density suspensions by using more than six passes.

As demonstrated in this experiment, plasmids and plasmid-containing cells may be processed in a bead mill using multiple passes without significant damage to the plasmids.

Discussion

Although cell disruption was accomplished by all the methods tested, only two methods, microfluidization and beadmilling resulted in high recovery of intact plasmid DNA. Sonication appeared to be very destructive to the DNA; even the mildest disruption conditions resulted in no intact DNA. Apparently, at least with the available sonication equipment, the shearing process is very rapid. This is consistent with the fact that sonication is often used to shear DNA, either for gene isolation and identification processes (Deininger, 1983) or for viscosity reduction in cell lysates. The failure of this method to produce intact plasmid DNA may be an inevitable result of the cavitation process believed to be the cause of cell disruption (Doulah, 1977), or may be a result of the fact that sonication is a localized process, taking place near the sonication horn. In order to get substantial cell disruption, cell suspensions must be processed for a relatively long time while the cells circulate near the sonicator horn. This probably results in significant co-destruction of the released plasmid DNA.

Nebulization resulted in a low recovery of plasmid DNA. The reason for this is not clear, because so little is known about the process. Apparently the atomization past the ceramic ball and/or the impact of the nebulizer mist droplets against the wall of the unit provides significant shear and results in DNA breakage. The kinetic models suggest that higher processing pressures increase the rate of the DNA destruction process more rapidly than the rate of DNA degradation resulting in lower maximum recoveries.

The Gaulin Mill, one of the most commonly used machines for cell disruption, severely degraded the DNA. Although there are a wide variety of configurations available and the opportunity to change processing conditions generally allows for optimization of the cell disruption process, little intact DNA was found here. One noteworthy feature is that the Gaulin Mill tends to produce rather small particles from whole cells (Agerkvist and Endfors, supra), probably indicating that it is a high shear (cavitation) process. In other words, the mill is more likely to reduce smaller particles to even smaller pieces than either the microfluidizer or the bead mill. This behavior seems to be consistent with the results here which showed that the Gaulin Mill resulted in almost no plasmid recovery under any conditions tested. Again the exact reason for the result is not known at this time.

The MICROFLUIDIZER® impinging-jet homogenizer performed better than any of the other pieces of equipment tested except the beadmnill. According to the manufacturer, the microfluidizer uses cavitation and shear produced by high speed intersection of two flowing suspension streams. The result is cell disruption without generation of very small particles. In the only other study available, *E. coli* cells were in general broken into two pieces (based on the average size of the debris) when processed through the device (Agerkvist and Endfors, supra).

Studies show that the high pressure tends to enhance the DNA degradation process relative to the cell disruption process, resulting in more cell disruption but lower plasmid DNA recoveries. The lower pressure system, operated at 1000 psi seemed to give a good combination of disruption and sheer rates. The high pressure system operated at similar low pressure (2000 psi) also achieved a similar satisfactory result. In summary, processing through either a lower pressure or higher pressure jet impingement device at a pressure around 2000 psi cell after one single pass through a single chamber resulted in good bacterial cell disruption and released up to 50% of intact plasmid DNA. These lower operating pressures are significantly different to what had been reported for protein recovery.

The most promising equipment tested was the DYNOM-ILL® (beadmill). A previous study (Agerkvist and Endfors, supra.) had shown that the particulates generated from the bead mill are relatively large, indicating a minimum of shear of already broken particles. Now we have discovered that this behavior extends to the shear effects on the plasmid molecules as very high plasmid recoveries were achieved under the right processing conditions.

The recovery achieved in the beadmill was related to the number of passes, the residence time of each pass, and the agitation speed or severity of the milling operation. High agitator speeds were more effective for cell disruption at the same residence time and number of passes through the device, but resulted in more plasmid destruction. Low recoveries were achieved at all residence times at high speed where cavitation is maximal. Under low agitation conditions, the recovery is much higher, apparently due to the lack of damage to intact plasmid DNA. This result is very different from that seen with other mechanical cell disruption devices, as well as in the bead mill at harsher operating conditions (e.g., higher rotation or agitation speeds). Consequently, a single one-pass mode of operation may be used instead of a multiple-pass mode of operation so long as similar total residence times are maintained. When plasmids are found to be susceptible to damage by the cell lysis operation, the multiple-pass mode is more desirable.

The pseudo rate constants used to represent the data from the bead mill suggest that the agitation speed has a different effect on the cell disruption rate than on the DNA degradation rate. In particular, the cell disruption rate appears to be mainly a function of the flow rate in the device (residence time). Disruption rate constants were about 0.5 per pass at high flow rates for both high and low speed runs. The value was about 1.5 at low flow rate in both high and low speed runs. This indicates that the residence time is the primary factor for cell disruption over the speed range tested. Conversely, the degradation rate constant was dependent primarily on the agitator speed. The rate constant jumped from less than 0.1 per pass at low speed to 0.8 per pass at high speed at the high flow rate and from 0.5 per pass to 3.0 per pass at the lower flow rate when the agitator speed was increased from low speed to high speed.

These findings suggest that a reduced agitation speed provides the best processing conditions for releasing intact plasmid DNA by bead mills. This will result in a reasonably high degree of cell disruption but a low amount of plasmid DNA degradation.

In summary, the mechanical cell disruption studies described here resulted in a clear distinction between various cell disruption methods in terms of the amount of intact plasmid DNA which survived the processing. Sonication, nebulization, and homogenization in the Gaulin Mill resulted in almost complete destruction of the plasmid DNA under any conditions sufficient to disrupt a substantial fraction of the cells. The impinging-jet homogenizer showed promise, up to 50% of the original plasmid DNA was released intact in the solution after mild processing with the low pressure system. The best processing method in terms of intact plasmid DNA recovery, however, was the bead mill, where over 90% of the plasmid DNA was solubilized without destruction under the low speed agitation conditions. It seems apparent that it is possible to provide cell disruption conditions which are not highly destructive to plasmid DNA.

I claim:

1. A mechanical method for disruption of plasmid-containing bacterial cells and release of intact plasmid DNA, comprising the steps of:
   a) passing liquid suspension of plasmid-containing bacterial cells through an impinging-jet homogenizer with a single interaction chamber at an operating pressure of about 750 to 4,000 psi, whereby the bacterial cells are disrupted and intact plasmid DNA is released, producing a liquid that contains intact plasmid DNA and disrupted bacterial cell debris; and,
   b) separating the disrupted bacterial cell debris from the liquid containing intact plasmid DNA.

2. A method of claim 1 wherein the operating pressure is about 1,000–3,000 psi.

3. A method of claim 2 wherein the operating pressure is about 2,000 psi.

4. A method of claim 1 wherein a MICROFLUIDIZER® impinging-jet homogenizer is used.

5. A method of claim 1 wherein the bacterial cells are *E. coli*.

6. A method of claim 5 wherein the bacterial cells are *E. coli* transfected with a recombinant plasmid capable of expressing a heterologous nucleic acid sequence of interest.

7. A method of claim 1 further comprising isolating the intact plasmid DNA.

8. The method of claim 1 further comprising the step of:
   passing said liquid that contains intact plasmid DNA and disrupted bacterial cell debris through an impinging-jet homogenizer with a single interaction chamber at an operating pressure of about 1,000 to 3,000 psi and recovering liquid that contains intact plasmid DNA and disrupted bacterial cell debris prior to
   separating the disrupted bacterial cell debris from the liquid containing intact plasmid DNA.

9. The method of claim 1 further comprising the steps of:
   twice passing said liquid that contains intact plasmid DNA and disrupted bacterial cell debris through an impinging-jet homogenizer with a single interaction chamber at an operating pressure of about 1,000 to 3,000 psi and recovering liquid that contains intact plasmid DNA and disrupted bacterial cell debris prior to
   separating the disrupted bacterial cell debris from the liquid containing intact plasmid DNA.

10. A mechanical method for disruption of plasmid-containing bacterial cells and release of intact plasmid DNA, comprising the steps of:
    a) passing liquid containing plasmid-containing bacterial cells through a bead mill containing beads of about 0.1 mm to about 1 mm in diameter, at an agitation speed of about 1,000 to 2,500 rpm, wherein the liquid is processed in the bead mill, for a total residence time in the bead mill of at least about 3 minutes, whereby bacterial cells are disrupted and intact plasmid DNA is released; and,
    b) separating the disrupted bacterial cell debris from the liquid containing intact plasmid DNA.

11. A method of claim 10 wherein the beads are about 0.25 mm to about 0.75 mm in diameter.

12. A method of claim 10 wherein the beads are about 0.5 mm in diameter.

13. A method of claim 10 wherein the beads are glass beads, ceramic beads, or stainless steel beads.

14. A method of claim 13 wherein the beads are glass beads.

15. A method of claim 10 wherein the agitation speed is about 2,000 rpm.

16. A method of claim 10 wherein the liquid is processed in the bead mill in a single-pass mode of operation.

17. A method of claim 16 wherein the total residence time of the liquid in the bead mill is about five (5) to about thirty five (35) minutes.

18. A method of claim 17 wherein the total residence time of the liquid in the bead mill is about ten (10) to about twenty (20) minutes.

19. A method of claim 10 wherein the liquid is processed in the bead mill using a multiple-pass mode of operation.

20. A method of claim 10 wherein the liquid is processed through the bead mill at least two times, for a residence time in the bead mill of about 0.5 to about 3 minutes per pass.

21. A method of claim 20 wherein the liquid is processed through the bead mill between four (4) and eight (8) passes, for a residence time in the bead mill of about 0.5 to about 3 minutes per pass.

22. A method of claim 21 wherein the liquid is processed through the bead mill between five (5) and six (6) passes, for a residence time in the bead mill of about 0.5 to about 3 minutes per pass.

23. A method of claim 10 wherein a DYNO®MILL bead mill is used.

24. A method of claim 10 wherein the bacteria are *E. coli*.

25. A method of claim 24 wherein the bacteria are *E. coli* transfected with a recombinant plasmid capable of expressing a heterologous nucleic acid sequence of interest.

26. A method of claim 10 further comprising isolating the intact plasmid DNA.

* * * * *